United States Patent
Berg et al.

(10) Patent No.: US 6,203,536 B1
(45) Date of Patent: *Mar. 20, 2001

(54) MEDICAL DEVICE FOR DELIVERING A THERAPEUTIC SUBSTANCE AND METHOD THEREFOR

(75) Inventors: Eric P. Berg, Plymouth; Thomas Q. Dinh, Minnetonka, both of MN (US)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,532

(22) Filed: Jun. 17, 1997

(51) Int. Cl.$^7$ ..................... A61M 31/00
(52) U.S. Cl. ............. 604/500; 604/502; 604/890.1; 427/2.12; 427/2.13; 427/2.31
(58) Field of Search .................. 623/1, 11, 12; 604/891.1, 53, 264, 280, 265, 890.1, 502, 500; 264/4, 48, 60, 81; 427/2.14, 2.12, 2.1, 2.16, 2.19, 2.21, 2.24, 2.13, 2.31

(56) References Cited

U.S. PATENT DOCUMENTS

| | | |
|---|---|---|
| 3,105,492 | 10/1963 | Jeckel . |
| 3,425,418 | 2/1969 | Chvapil et al. . |
| 3,451,996 | 6/1969 | Sumyk et al. . |
| 3,523,807 | 8/1970 | Gerendas . |
| 3,549,409 | 12/1970 | Dyck . |
| 3,688,317 | 9/1972 | Kurtz . |
| 4,188,188 | 2/1980 | Willner et al. . |
| 4,229,540 | 10/1980 | Coan . |
| 4,229,838 * | 10/1980 | Mano ..................... 3/1.4 |
| 4,321,711 * | 3/1982 | Mano ..................... 3/1.4 |
| 4,540,573 | 9/1985 | Neurath et al. . |
| 4,548,736 | 10/1985 | Miller et al. . |
| 4,613,665 | 9/1986 | Larm . |

(List continued on next page.)

FOREIGN PATENT DOCUMENTS

| | | |
|---|---|---|
| 0 366 564 A2 | 5/1990 | (EP) . |
| WO 86/06729 | 11/1986 | (WO) . |
| WO 89/07932 | 9/1989 | (WO) . |
| WO 91/12779 | 9/1991 | (WO) . |
| WO 94/17108 | 8/1994 | (WO) . |
| WO 94/27612 | 12/1994 | (WO) . |
| WO 97/42911 | 11/1997 | (WO) . |

OTHER PUBLICATIONS

Dyck, "Inorganic Heparin Complexes for the Preparation of Nonthrombogenic Surfaces", *J. Biomed. Mater. Res.*, 6, pp. 115–141 (1972).

(List continued on next page.)

*Primary Examiner*—Wynn Wood Coggins
*Assistant Examiner*—Jeremy Thisseu
(74) *Attorney, Agent, or Firm*—Sterne, Kessler, Goldstein & Fox P.L.L.C.

(57) ABSTRACT

A device useful for localized delivery of a therapeutic material is provided. The device includes a structure including a porous material; and a water-insoluble salt of a therapeutic material dispersed in the porous material. The water-insoluble salt is formed by contacting an aqueous solution of a therapeutic salt with a heavy metal water-soluble salt dispersed throughout a substantial portion of the porous material. The heavy metal water-soluble salt can be dispersed in the porous material so that the device can be sterilized and the therapeutic material can be loaded in the device in situ, for example, just prior to use. The therapeutic material is preferably a heparin or heparin derivative or analog which renders the material antithrombotic as an implantable or invasive device.

11 Claims, 4 Drawing Sheets

(1 of 4 Drawing Sheet(s) Filed in Color)

U.S. PATENT DOCUMENTS

| | | |
|---|---|---|
| 4,623,539 | 11/1986 | Tunc . |
| 4,680,177 | 7/1987 | Gray et al. . |
| 4,733,665 | 3/1988 | Palmaz . |
| 4,768,507 | 9/1988 | Fischell et al. . |
| 4,800,882 | 1/1989 | Gianturco . |
| 4,873,308 | 10/1989 | Coury et al. . |
| 4,886,062 | 12/1989 | Wiktor . |
| 5,010,063 | 4/1991 | Piani et al. . |
| 5,039,529 | 8/1991 | Bergendal et al. . |
| 5,059,166 | 10/1991 | Fischell et al. . |
| 5,061,276 * | 10/1991 | Tu et al. ................................. 623/1 |
| 5,104,860 | 4/1992 | Piani et al. . |
| 5,342,605 | 8/1994 | Illig . |
| 5,352,434 | 10/1994 | Illig et al. . |
| 5,399,318 | 3/1995 | Mancilla et al. . |
| 5,451,424 * | 9/1995 | Solomon et al. . |
| 5,464,650 | 11/1995 | Berg et al. . |
| 5,510,077 | 4/1996 | Dinh et al. . |
| 5,531,735 * | 7/1996 | Thompson ........................ 604/891.1 |
| 5,541,305 | 7/1996 | Yokota et al. . |
| 5,554,182 | 9/1996 | Dinh et al. . |
| 5,571,166 | 11/1996 | Dinh et al. . |
| 5,591,227 | 1/1997 | Dinh et al. . |
| 5,599,352 | 2/1997 | Dinh et al. . |
| 5,609,629 * | 3/1997 | Fearnot et al. ..................... 604/53 X |
| 5,624,411 | 4/1997 | Tuch . |
| 5,679,400 | 10/1997 | Tuch . |
| 5,697,967 | 12/1997 | Dinh et al. . |
| 5,716,981 | 2/1998 | Hunter et al. . |
| 5,776,184 | 7/1998 | Tuch . |
| 5,848,995 * | 12/1998 | Walder ................................. 604/265 |
| B1 4,733,665 | 1/1994 | Palmaz . |

OTHER PUBLICATIONS

Lincoff et al., "Intercoronary Stenting Compared with Conventional Therapy for Abrupt Vessel Closure Complicating Coronary Angioplasty", *J. Am. Coll. Cardiol.*, 21, pp. 866–875, 1993.

Van Beusekom et al., "Synthetic polymers as an alternative to metal in stens? In vivo and mechnical behaviour of polyethylene–terephtalate", *Circulation*, 86 (supp. I), pp. I–731, No. 2912, 1992.

Fischell et al., "Low–Dose β–Particle Emission From 'Stent' Wire Results in Complete, Localized Inhibition of Smooth Muscle Cell Proliferation", *Circulation*, 90:2956–2963 (1994).

Waksman et al., "Endovascular Low–Dose Irradiation Inhibits Neointima Formation After Coronary Artery Balloon Injury in Swine. A Possible Role for Radiation Therapy in Restenosis Prevention", *Circulation*, 91:1533–1539 (1995).

Liu et al., "Porous polyurethane vascular prostheses with variable compliances", *J. Biomed. Mater. Res.*, 26 pp. 1489 (1992).

McNair, "Using Hydrogel Polymers for Drug Delivery", *Medical Device Technology*, pp. 16–22, (1966).

"Photolink Surface Modification Technical Bulletin: Heparin Coatings For Medical Devices", *Brochure from BSI Surface Modification Sciences*, (1994).

William D. Spotnitz et al., "Fibrin Glue from Stored Human Plasma. An Inexpensive and Efficient Method for Local Blood Bank Preparation", *The American Surgeon*, 53, 460–462 (1987).

K. Whang et al., "A novel method to fabricate bioabsorbable scaffolds", *Polymer*, 36:4, 837–842 (1995).

* cited by examiner

MEDICAL DEVICE FOR DELIVERING A THERAPEUTIC SUBSTANCE AND METHOD THEREFOR

BACKGROUND OF THE INVENTION

This invention relates to a medical device employing a therapeutic substance as a component thereof. For example in an arterial site treated with percutaneous transluminal coronary angioplasty therapy for obstructive coronary artery disease a therapeutic antithrombogenic substance such as heparin may be included with a device and delivered locally in the coronary artery. Also provided is a method for making a medical device capable of localized application of therapeutic substances.

Medical devices which serve as substitute blood vessels, synthetic and intraocular lenses, electrodes, catheters and the like in and on the body or as extracorporeal devices intended to be connected to the body to assist in surgery or dialysis are well known. For example, intravascular procedures can bring medical devices into contact with the patient's vasculature. In treating a narrowing or constriction of a duct or canal percutaneous transluminal coronary angioplasty (PTCA) is often used with the insertion and inflation of a balloon catheter into a stenotic vessel. Other intravascular invasive therapies include atherectomy (mechanical systems to remove plaque residing inside an artery), laser ablative therapy and the like. However, this use of mechanical repairs can have adverse consequences for the patient. For example, restenosis at the site of a prior invasive coronary artery disease therapy occurs in a majority of cases. Restenosis, defined angiographically, is the recurrence of a 50% or greater narrowing of a luminal diameter at the site of a prior coronary artery disease therapy, such as a balloon dilatation in the case of PTCA therapy. In particular, an intra-luminal component of restenosis develops near the end of the healing process initiated by vascular injury, which then contributes to the narrowing of the luminal diameter. This phenomenon is sometimes referred to as "intimal hyperplasia." It is believed that a variety of biologic factors are involved in restenosis, such as the extent of the injury, platelets, inflammatory cells, growth factors, cytokines, endothelial cells, smooth muscle cells, and extracellular matrix production, to name a few.

Attempts to inhibit or diminish restenosis often include additional interventions such as the use of intravascular stents and the intravascular administration of pharmacological therapeutic agents. Examples of stents which have been successfully applied over a PTCA balloon and radially expanded at the same time as the balloon expansion of an affected artery include the stents disclosed in U.S. Pat. No. 4,733,665 issued to Palmaz, U.S. Pat. No. 4,800,882 issued to Gianturco and U.S. Pat. No. 4,886,062 issued to Wiktor. Also, such stents employing therapeutic substances such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents have been considered for their potential to solve the problem of restenosis.

Another concern with intravascular and extracorporeal procedures is the contact of biomaterials with blood which can trigger the body's hemostatic process. The hemostatic process is normally initiated as the body's response to injury. When a vessel wall is injured, platelets adhere to damaged endothelium or exposed subendothelium. Following adhesion of the platelets, these cells cohere to each other preparatory to aggregation and secretion of their intracellular contents. Simultaneously there is activation, probably by electrostatic charge of the contact factors, of the coagulation cascade. The sequential step-wise interaction of these procoagulant proteins results in the transformation of soluble glycoproteins into insoluble polymers, which after transamidation results in the irreversible solid thrombus.

Immobilization of polysaccharides such as heparin to biomaterials has been used to improve bio- and hemocompatibility of implantable and extracorporeal devices. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, immobilization of heparin to a biomaterial surface consists of activating the material in such a way that coupling between the biomaterial and functional groups on the heparin (—COOH, —OH, —$NH_2$) can be achieved. For example, Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generation of thrombi and microemboli.

However, the attachment and delivery of therapeutic substances such as heparin can involve complicated and expensive chemistry. It is therefore an object of the present invention to provide a medical device having a biocompatible, blood-contacting surface with an active therapeutic substance at the surface and a simple, inexpensive method for producing such a surface.

SUMMARY OF THE INVENTION

This invention relates to a medical device having a blood-contacting surface with a therapeutic substance thereon. Preferably, the device according to the invention is capable of applying a highly localized therapeutic material into a body lumen to treat or prevent injury. The term "injury" means a trauma, that may be incidental to surgery or other treatment methods including deployment of a stent, or a biologic disease, such as an immune response or cell proliferation caused by the administration of growth factors. In addition, the methods of the invention may be performed in anticipation of "injury" as a prophylactic. A prophylactic treatment is one that is provided in advance of any symptom of injury in order to prevent injury, prevent progression of injury or attenuate any subsequent onset of a symptom of such injury.

In accordance with the invention, a device for delivery of localized therapeutic material includes a structure including a porous material and a plurality of discrete particles of a water-insoluble salt of the therapeutic material dispersed throughout a substantial portion of the porous material. Preferably, the device is capable of being implanted in a body so that the localized therapeutic agent can be delivered in vivo, typically at a site of vascular injury or trauma. More preferably, the porous material is also biocompatible, sufficiently tear-resistant and nonthrombogenic.

The porous material may be a film on at least a portion of the structure or the porous material may be an integral portion of the structure. Preferably, the porous material is selected from the group of a natural hydrogel, a synthetic hydrogel, teflon, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like.

The therapeutic agent preferably includes an antithrombotic material. More preferably, the antithrombotic material is a heparin or heparin derivative or analog. Also preferably, the insoluble salt of the therapeutic material is one of the silver, barium or calcium salts of the material.

The structure of the device can be adapted for its intended extracorporeal or intravascular purpose in an internal human body site, such as an artery, vein, urethra, other body lumens, cavities, and the like or in an extracorporeal blood pump, blood filter, blood oxygenator or tubing. In one aspect of the invention, the shape is preferably generally cylindrical, and more preferably, the shape is that of a catheter, a stent, or a guide wire.

In another aspect of the invention, an implantable device capable of delivery of a therapeutic material includes a structure comprising a porous material; and a plurality of discrete particles comprising a heavy metal water-soluble salt dispersed throughout a substantial portion of the porous material. Preferably, the heavy metal water-soluble salt is selected from the group of $AgNO_3$, $Ba(NO_3)_2$, $BaCl_2$, and $CaCl_2$. The amount of water-soluble salt dispersed throughout a portion of the porous material determines the total amount of therapeutic material that can be delivered once the device is implanted.

The invention also provides methods for making an implantable device which includes therapeutic materials. In one embodiment, a method of the invention includes loading a structure comprising a porous material with a heavy metal water-soluble salt dispersed throughout a substantial portion of the porous material, sterilizing the loaded structure, and packaging for storage and, optionally, delivery of the sterilized loaded structure. Preferably, the method of the invention further includes substantially contemporaneously loading of a water soluble therapeutic material, wherein a water insoluble salt of the therapeutic material is produced throughout a substantial portion of the porous material of the structure. "Substantially contemporaneously," means that the step of loading a water soluble therapeutic material occurs at or near a step of positioning the device proximate to a desired area, i.e., at or near the surgical arena prior to administration to or implantation in, a patient. More preferably, the water insoluble salt of the therapeutic material is dispersed throughout a substantial portion of the porous material.

In another aspect of the invention, a method includes loading a structure comprising a porous material with a heavy metal water-soluble salt dispersed throughout a substantial portion of the porous material; loading a water soluble therapeutic material, wherein a water insoluble salt of the therapeutic material is produced in a substantial portion of the porous material of the structure; and packaging for delivery of the loaded structure.

Thus, the methods for making an implantable device to deliver a therapeutic material and device in vivo, or in an extracorporeal circuit in accordance with the invention, are versatile. A therapeutic material may be loaded onto a structure including a porous material at any number of points between, and including, the point of manufacture and the point of use. As a result of one method, the device can be stored and transported prior to incorporation of the therapeutic material. Thus, the end user can select the therapeutic material to be used from a wider range of therapeutic agents.

BRIEF DESCRIPTION OF THE DRAWINGS

The file of this patent contains at least one drawing executed in color. Copies of this patent with color drawings are provided to the Patent and Trademark Office with payment of the necessary fee.

DESCRIPTION OF PREFERRED EMBODIMENTS

One of the more preferred configurations for a device according to the invention is a stent for use in artery/vascular therapies. The term "stent" refers to any device capable of being delivered by a catheter and which, when placed into contact with a portion of a wall of a lumen to be treated, will also deliver localized therapeutic material at a luminal or blood-contacting portion of the device. A stent typically includes a lumen wall-contacting surface and a lumen-exposed surface. Where the stent is shaped generally cylindrical or tube-like, including a discontinuous tube or ring-like structure, the lumen-wall contacting surface is the surface in close proximity to the lumen wall whereas the lumen-exposed surface is the inner surface of the cylindrical stent. The stent can include polymeric or metallic elements, or combinations thereof, onto which a porous material is applied. For example, a deformable metal wire stent is useful as a stent framework of this invention, such as that described in U.S. Pat. No. 4,886,062 to Wiktor, which discloses preferred methods for making a wire stent. Other metallic stents useful in this invention include those of U.S. Pat. No. 4,733,655 to Palmaz and U.S. Pat. No. 4,800,882 to Gianturco.

Figure 1:
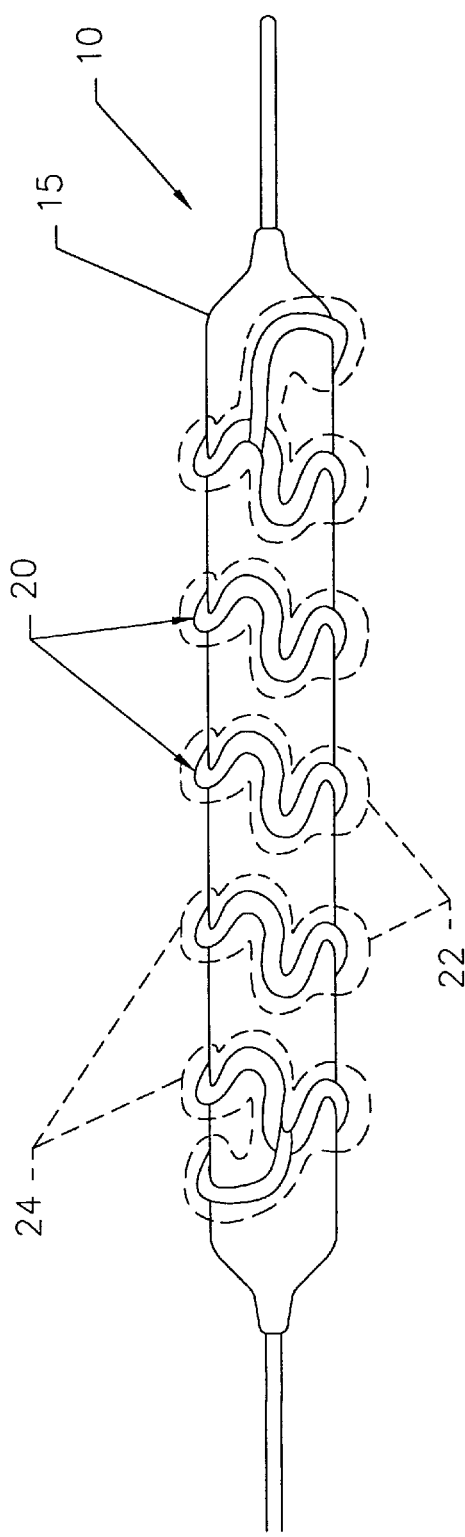
FIG. 1 is an elevational view of one embodiment of a device according to the invention with a balloon catheter as a mode of delivery of the device.

Referring now to FIG. 1, the stent 20 comprises a stent framework 22 and a porous material coating 24. The stent framework 22 is deformable and can be formed from a polymeric material, a metal or a combination thereof. A balloon 16 is positioned in FIG. 1 adjacent the lumen-exposed surface of the stent to facilitate delivery of the stent. The stent 20 can be modified to increase or to decrease the number of wires provided per centimeter in the stent framework 22. Similarly, the number of wire turns per centimeter can also be modified to produce a stiffer or a more flexible stent framework.

Polymeric stents can also be used in this invention. The polymers can be nonbioabsorbable or bioabsorbable in part, or total. Stents of this invention can be completely nonbioabsorbable, totally bioabsorbable or a composite of bioabsorbable polymer and nonabsorbable metal or polymer. For example, another stent suitable for this invention includes the self-expanding stent of resilient polymeric material as disclosed in International Publication No. WO 91/12779.

Nonbioabsorbable polymers can be used as alternatives to metallic stents. The stents of this invention should not substantially induce inflammatory and neointimal responses. Examples of biostable nonabsorbable polymers that have been used for stent construction with or without metallic elements include polyethylene terephthalate (PET), polyurethane urea and silicone (for example, see van Beusekom et al. *Circulation* 86(supp. I):I-731, 1992 and Lincoff et al. *J. Am. Coll Cardiol* 21(supp. 1):335A, 1994. Although the porous material is shown as a coating 24, it is to be understood that, for the purposes of this invention, the porous material can be incorporated into the material of the stent.

Figure 2:
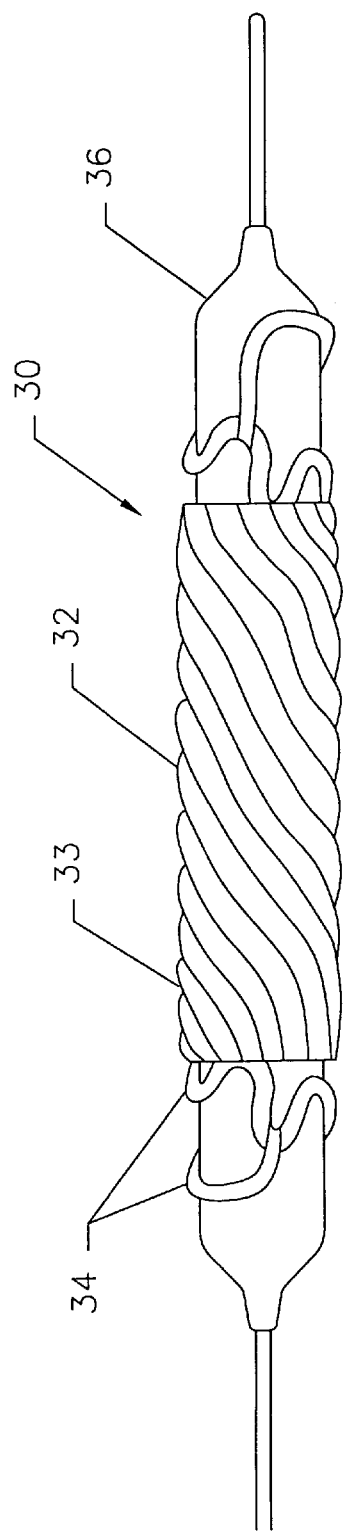
FIG. 2 is an elevational view of another embodiment of a device according to the invention with a balloon catheter as a mode of delivery of the device.

Referring to FIG. 2, an alternative stent 30 is shown. The stent framework 34 is affixed with a film of a porous material 32. This can be accomplished by wrapping the film 32 around the stent framework 34 and securing the film 32 to the framework 34 (i.e., the film is usually sufficiently tacky to adhere itself to the framework but a medical grade adhesive could also be used if needed) so that the film 32 will stay on the balloon 36 and framework 34 until it is delivered to the site of treatment. The film 32 is preferably wrapped over the framework with folds or wrinkles that will allow the stent 30 to be readily expanded into contact with the wall of the lumen to be treated. Preferably, the film 32 is located on a lumen-wall contacting surface 33 of the stent framework 34 such that radiation is substantially locally delivered to a lumen wall, for example, an arterial wall membrane (not shown).

Porous Material

As mentioned above, the device according to the invention is generally a structure including a porous material. In one embodiment, the porous material is a film on at least a portion of the structure. In another embodiment, the porous material is an integral portion of the structure. Preferably, the porous material is biocompatible, and sufficiently tear-resistant and nonthrombogenic. More preferably, the porous material is selected from the group of a natural hydrogel, a synthetic hydrogel, teflon, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like. In materials which do not include pores in their usual structural configurations, pores between one micrometer in diameter or as large as 1000 micrometers in diameter can be introduced by conventional means such as by introducing a solvent soluble particulate material into the desired structure and dissolving the particulate material with a solvent. However, no particular pore size is critical to this invention.

Therapeutic Material

The therapeutic material used in the present invention could be virtually any therapeutic substance which possesses desirable therapeutic characteristics and which can be provided in both water soluble and water insoluble salts and which have bioactivity as an insoluble salt. For example, antithrombotics, antiplatelet agents, antimitotic agents, antioxidants, antimetabolite agents, anti-inflammatory agents and radioisotopes could be used. "Insoluble salt" or "water insoluble salt" of the therapeutic substance as set forth herein, means that the salt formed has a relatively poor solubility in water such that it will not readily disperse from the pores of the device. In particular, anticoagulant agents such as heparin, heparin derivatives and heparin analogs could be used to prevent the formation of blood clots on the device. Also, water-insoluble radioactive salts such as $AgI^{125}$, $BaS^{35}O_4$, and $(Ca)_3(P^{32}O_4)_2$ could be used for application of radiotherapy to a body lumen or blood.

Preferably, the water-insoluble salt of the therapeutic material is formed by a heavy metal water-soluble salt interacting with an aqueous radioactive salt solution. In the present invention, the heavy metal water-soluble salt is dispersed throughout a substantial portion of the porous material. Preferably, the heavy metal water-soluble salt is selected from the group of $AgNO_3$, $Ba(NO_3)_2$, $BaCl_2$, $CaCl_2$, and a mixture thereof. The amount of water-soluble salt dispersed throughout a portion of the porous material determines the ultimate amount of therapeutic material capable of being administered once the device is implanted.

Methods of Making an Implantable Device

Figure 3:
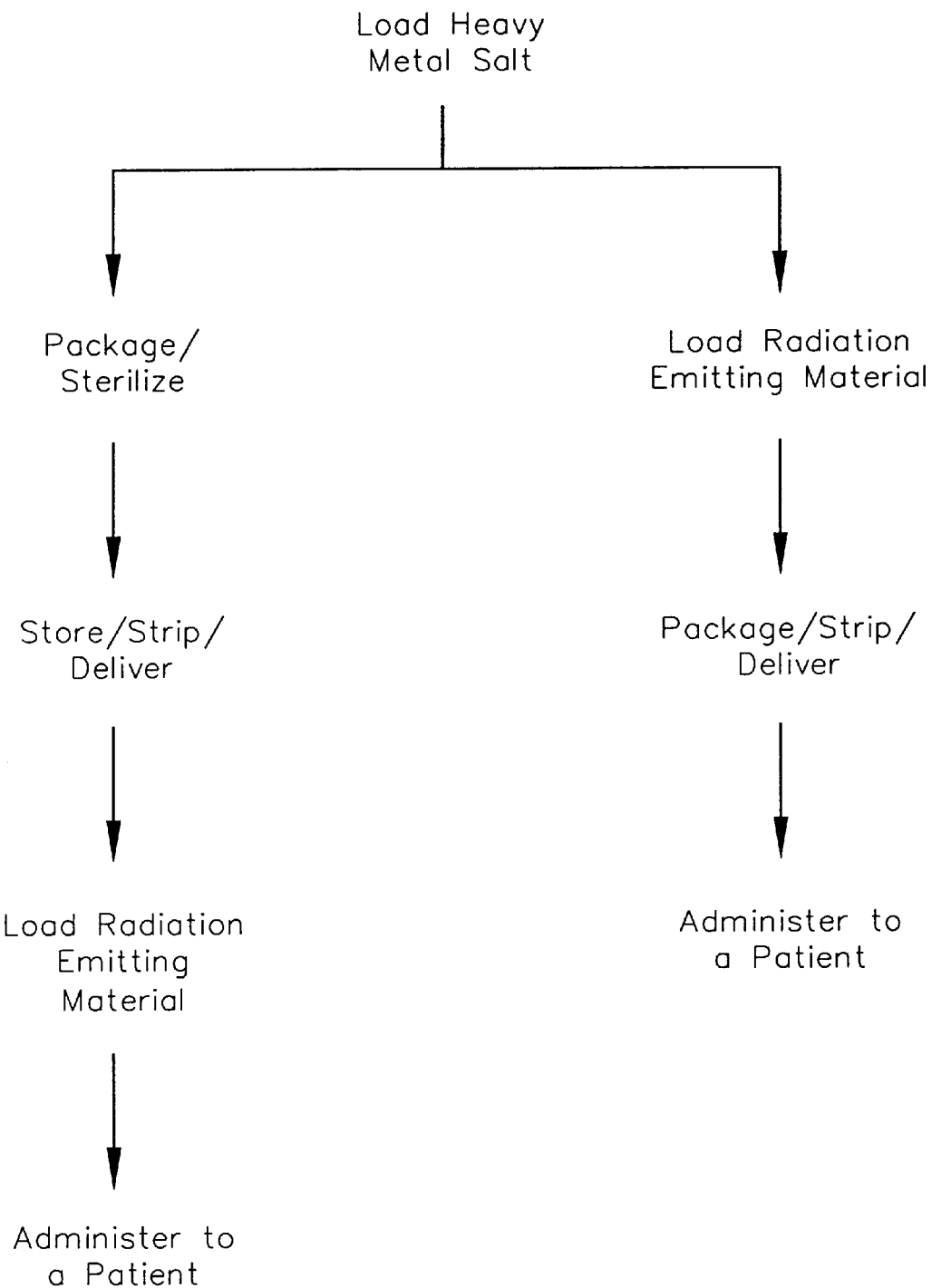
FIG. 3 is a flow diagram schematically illustrating methods according to the invention.

Referring now to FIG. 3, a structure having a porous material is loaded with a heavy metal water-soluble salt. Preferably, this step includes contacting, more preferably immersing, the structure with an aqueous solution of the heavy metal water-soluble salt, as described above. Preferably, the heavy metal water-soluble salt is dispersed throughout a substantial portion of the porous material. This may be assisted by degassing the pores of the structure by such techniques as ultrasound or vacuum degassing. The resulting structure can now be sterilized, packaged and, optionally, stored until use.

In one embodiment of the invention, a sterilized structure is shipped or delivered to the relevant consumer. The structure is substantially contemporaneously loaded with a water soluble therapeutic material. Preferably, the loading of the therapeutic material includes contacting, more preferably immersing, the porous material in an aqueous solution comprising a salt of the therapeutic material, as described above. Again, degassing of the device can help to bring the therapeutic material into the pores. A water-insoluble therapeutic salt is thereby formed within the porous material. Examples of aqueous radioactive salt solutions for radiotherapy include $NaI^{125}$, $K_2S^{35}O_4$, $NaS^{35}O_4$, and $Na_3P^{32}O_4$, to name a few.

This method is advantageous in that the structure can be loaded with the therapeutic material in situ, i.e., at or near the point of therapeutic use, typically before administration, preferably implantation, to a patient. This is particularly useful because the device can be stored and transported prior to incorporation of the therapeutic material. This feature has several advantages. For example, the relevant consumer can select the therapeutic material to be used from a wider range of therapeutic materials, e.g., a radioisotope with a certain half-life with certain particle emitting characteristics can be selected. Thus, the therapeutic material selected is not limited to only those supplied with the device but can instead be applied according to the therapy required.

In another aspect of the invention, a sterilized structure is loaded with a therapeutic material. Preferably, the loading of the therapeutic material includes contacting, more preferably immersing, the porous material in an aqueous solution comprising a salt of the therapeutic material, wherein a water-insoluble salt of the therapeutic material is formed within the porous material. Examples of therapeutic salt solutions may be those previously mentioned above. The structure is preferably packaged and can shipped to the relevant consumer. The structure can now be administered, preferably implanted, to a patient. Thus, in this embodiment, the structure is loaded with the therapeutic material prior to reaching the point of use, which may be more convenient depending upon the facilities available to the relevant consumer.

The following non-limiting examples will further illustrate the invention. All parts, percentages, ratios, etc. are by weight unless otherwise indicated.

Example 1

The following solutions were used in the procedure:

Solution A: 1–10% aqueous solution of $BaCl_2$

Solution B: 1–10% aqueous solution of $Ba(NO_3)_2$

Solution C: 1–10% aqueous solution of $Na_2S^{35}O_4$

A gamma-radiation sterilized porcine fibrin stent made according to U.S. Pat. No. 5,510,077 was treated by rehydration in Solution A by immersion for about 5 to about 10 minutes. The stent was removed and excess solution was blotted with absorbent paper. The stent was then dehydrated and sterilized by gamma radiation.

This treated stent was then rehydrated in an aqueous solution of $Na_2S^{35}O_4$ radioisotope having a specific activity of about $10\mu$ Ci/ml to about $500\mu$ Ci/ml. A white precipitate of $BaS^{35}O_4$ was observed within the pores of the stent surface. The stent can now be implanted into an artery for localized delivery of radiation or packaged for delivery to the consumer.

Example 2

Figure 4:
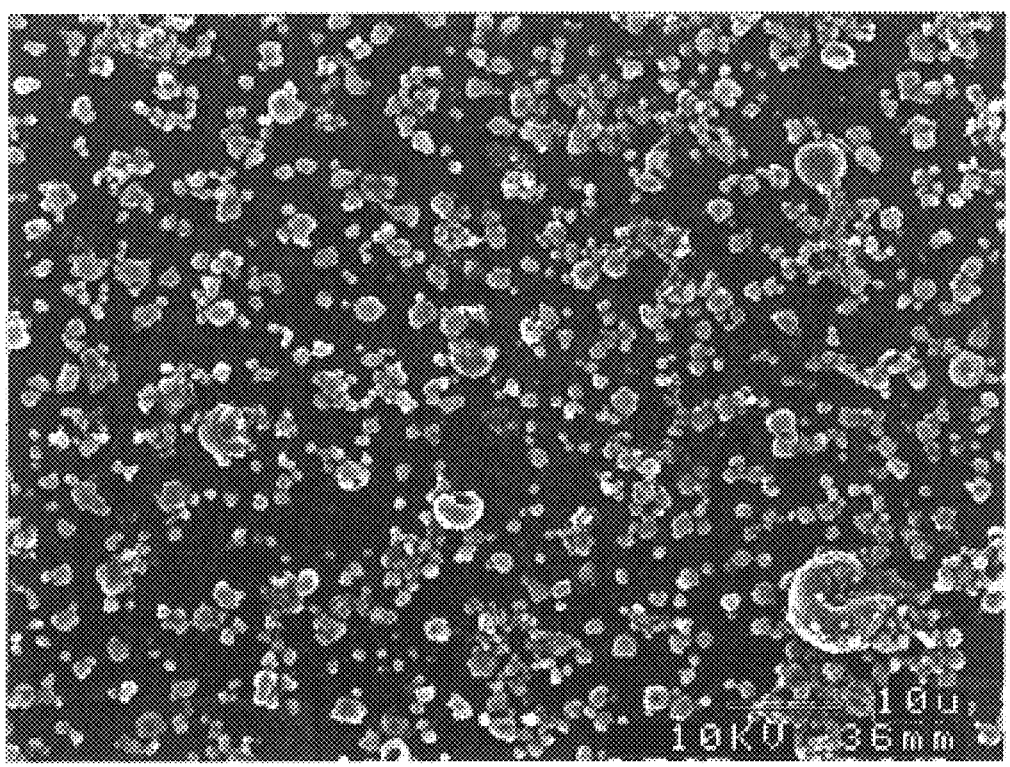
FIG. 4 is a photograph taken from a scanning electron microscope of a surface showing the insoluble therapeutic material according to the invention.
Figure 5A:
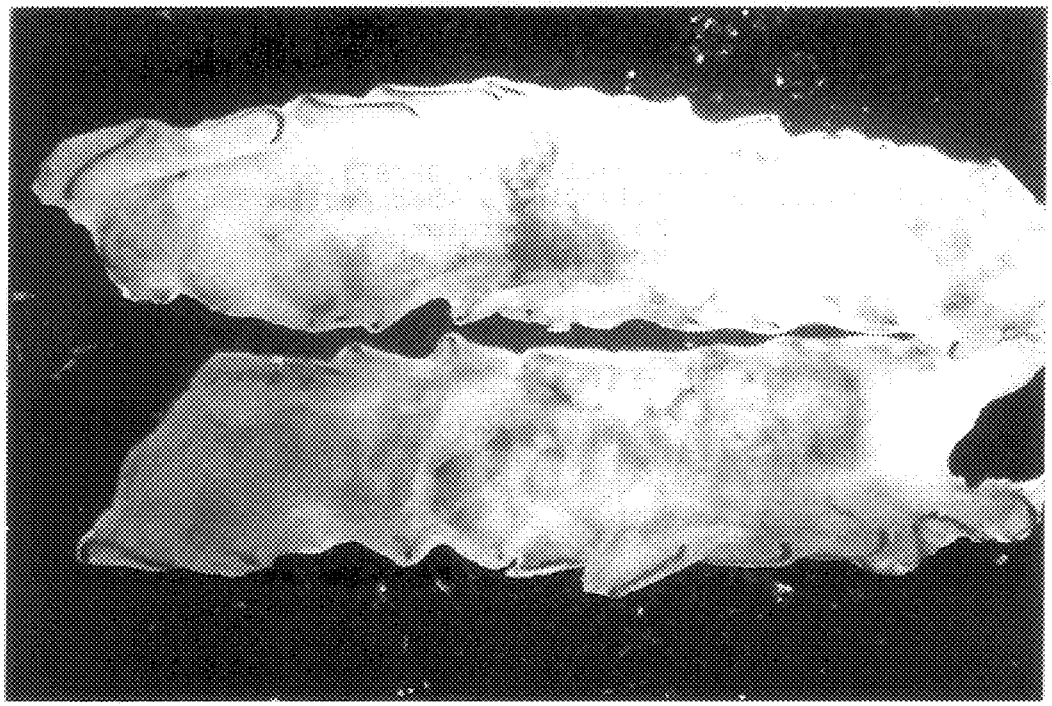
FIGS. 5a and 5b are photographs showing the histological comparison between a stent heparinized according to the present invention (5a) and a control stent (5b).
Figure 5B:
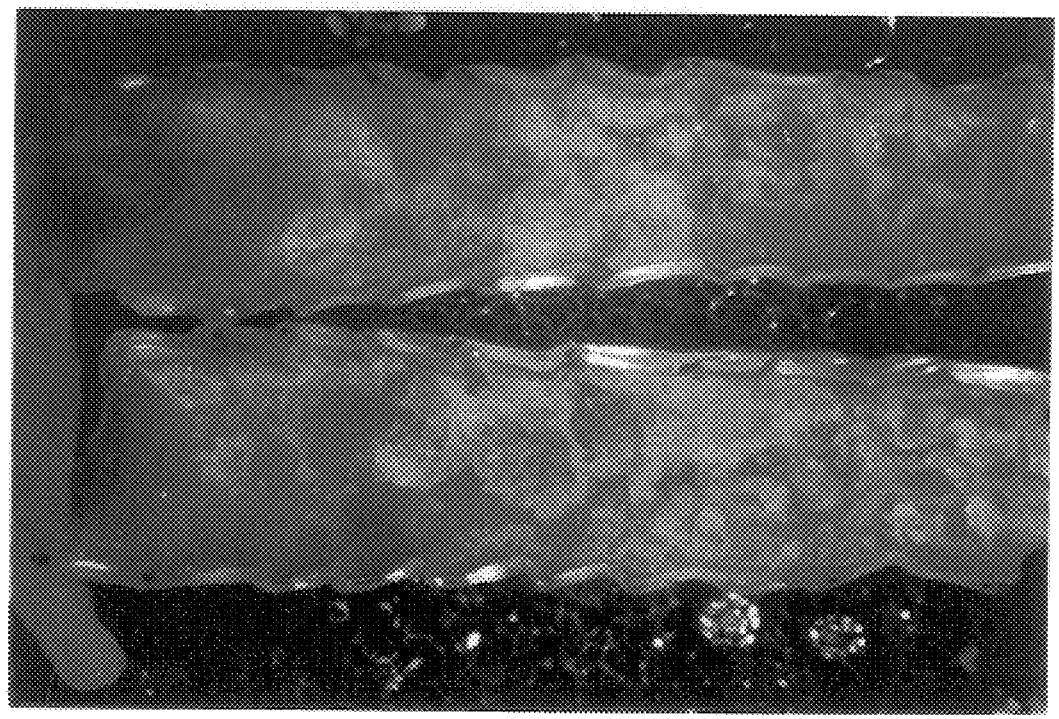

Fibrin stents made according to U.S. Pat. No. 5,510,077 were soaked in a 20% by weight solution of $BaCl_2$ (preferably soaking for about 10 to 30 minutes). The stents were then subjected to degassing by vacuum to remove air from the pores of the fibrin matrix, thus allowing the $BaCl_2$ solution to fill the pores. The stents were dried overnight. The dried stents were placed into a solution of sodium heparinate (preferably soaking in a solution of 1000 U/ml to 20,000 U/ml for 10–20 minutes—most preferably a solution of at least 10,000 U/ml) to allow the $BaCl_2$ in the fibrin matrix to react with the sodium heparinate to form barium heparinate which was precipitated within the fibrin matrix. Scanning electron microscopy (SEM) showed that particulates of barium heparinate in the order of 10 microns and smaller were trapped within the fibrin matrix (FIG. 4). In vivo evaluation of the barium heparinate stents were carried out using a carotid crush model in pigs with standard fibrin stents as controls. After 24 hours, the stents were compared for flow and were then examined histologically. While flow did not differ in a statistically significant manner between the control stent and the barium heparinate stent, the histological study showed substantially reduced clot formation on the barium heparinate stent (FIG. 5a) when compared with the control stent (FIG. 5b).

The complete disclosures of all patents, patent applications, and publications referenced herein are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

We claim:

1. A method for making a medical device having a blood-contacting surface comprising the steps of:

providing a structure having a blood-contacting surface of a porous material;

loading a heavy metal water-soluble salt throughout a substantial portion of the porous material; and contacting the blood-contacting surface of the structure with a water soluble therapeutic material, wherein a heavy metal water insoluble salt of the therapeutic material is formed within at least a portion of the porous material.

2. The method of claim 1 wherein the heavy metal water insoluble salt of the therapeutic material comprises a salt of an antithrombotic material.

3. The method of claim 2 wherein the antithrombotic material is heparin.

4. The method of claim 1 wherein the porous material is selected from the group consisting of a natural hydrogel, a synthetic hydrogel, teflon, silicone, polyurethane, polysulfone, cellulose, polyethylene, polypropylene, polyamide, polyester, polytetrafluoroethylene, and a combination of two or more of these materials.

5. The method of claim 4 wherein the natural hydrogel is fibrin.

6. The method of claim 1 wherein loading the therapeutic material is performed substantially contemporaneously with administration of the structure to a patient.

7. The method of claim 1 wherein the water insoluble salt of the therapeutic material comprises a salt of an antithrombotic, an antiplatelet agent, an anticoagulant agent, an antimitotic agent, an antioxidant, and antimetabolite agent, or an anti-inflammatory agent.

8. The method of claim 1 wherein the therapeutic material is effective to treat or prevent restenosis.

9. The method of claim 1 wherein the heavy metal water-insoluble salt of the therapeutic material comprises at least one salt selected from the group consisting of a silver salt, a barium salt, and a calcium salt.

10. The method of claim 1 wherein the porous material comprises a film.

11. The method of claim 1 wherein the porous material comprises an integral portion of the device.

* * * * *